(12) United States Patent
Cheng et al.

(10) Patent No.: US 7,786,338 B2
(45) Date of Patent: Aug. 31, 2010

(54) SELECTIVE OLIGOMERIZATION OF ISOBUTENE

(75) Inventors: Jane C. Cheng, Bridgewater, NJ (US); Ivy D. Johnson, Lawrenceville, NJ (US); Wieslaw J. Roth, Sewell, NJ (US); Michael C. Kerby, Center Valley, PA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 522 days.

(21) Appl. No.: 11/977,977

(22) Filed: Oct. 26, 2007

(65) Prior Publication Data

US 2009/0112036 A1    Apr. 30, 2009

(51) Int. Cl.
  *C07C 2/04*    (2006.01)
(52) U.S. Cl. ......................... 585/533; 585/510
(58) Field of Classification Search ................ None
  See application file for complete search history.

(56) References Cited

U.S. PATENT DOCUMENTS

| | | |
|---|---|---|
| 3,354,078 A | 11/1967 | Miale et al. |
| 4,439,409 A | 3/1984 | Puppe et al. |
| 4,826,667 A | 5/1989 | Zones et al. |
| 4,954,325 A | 9/1990 | Rubin et al. |
| 5,236,575 A | 8/1993 | Bennett et al. |
| 5,250,277 A | 10/1993 | Kresge et al. |
| 5,362,697 A | 11/1994 | Fung et al. |
| 6,077,498 A | 6/2000 | Cabanas et al. |
| 6,914,166 B2 | 7/2005 | Dakka et al. |
| 7,112,711 B2 | 9/2006 | Mathys et al. |
| 2007/0213576 A1 | 9/2007 | Brown et al. |

FOREIGN PATENT DOCUMENTS

| | | |
|---|---|---|
| EP | 0293032 B1 | 7/1993 |
| WO | WO 97/17290 | 5/1997 |
| WO | WO 2005/118476 A1 | 5/2005 |

*Primary Examiner*—In Suk Bullock
(74) *Attorney, Agent, or Firm*—Robert A. Migliorin

(57) ABSTRACT

A process for oligomerizing isobutene includes contacting a feedstock including isobutene with a catalyst comprising an EMM-10 molecular sieve under conditions effective to oligomerize said isobutene and produce an effluent containing less isobutene than the feedstock.

23 Claims, 2 Drawing Sheets

SELECTIVE OLIGOMERIZATION OF ISOBUTENE

FIELD

The present invention relates to the selective oligomerization of isobutene.

BACKGROUND

The selective oligomerization of isobutene is an important chemical reaction, particularly where the isobutene is contained in a refinery $C_4$ hydrocarbon stream, such as Raffinate-1 and Raffinate-2.

For example, $C_4$ linear olefins are an attractive feedstock for producing octenes with zeolite catalysts because, among other reasons, the resulting octenes have triple branching of less than about 5 wt %. However, when isobutene is present in significant quantities (>10 wt %) in the oligomerization feedstock, such as with Raffinate-1, the amount of triple-branched octenes increases to a level which is unacceptable for some end uses such as certain plasticizers. In the past, this problem was generally addressed by selectively reacting the isobutene with methanol to produce methyl t-butyl ether (MTBE). However, with the phase-out of MTBE because of environmental concerns, this reaction is no longer an attractive method of removing isobutene. As a result, interest has focused on selective dimerization of the isobutene to produce octenes useful as, for example, gasoline octane enhancers and as feedstocks for producing $C_9$ aldehydes and/or alcohols.

Another use for the selective oligomerization of isobutene is in the purification of $C_4$ olefin streams used in the alkylation of benzene to produce sec-butylbenzene, an important precursor in the production of phenol. Thus, even when present at only low levels (<5 wt %) in a $C_4$ olefin stream, such as Raffinate-2, isobutene reacts with benzene to produce tert-butylbenzene. However, tert-butylbenzene is difficult to separate from sec-butylbenzene by distillation since the boiling points of the two butylbenzene isomers are very similar, 169° C. for tert-butylbenzene as compared with 173° C. for sec-butylbenzene. Moreover, tert-butylbenzene is known to be an inhibitor to the oxidation of sec-butylbenzene to the corresponding hydroperoxide, which is the first step in the conversion of sec-butylbenzene to phenol and methyl ethyl ketone.

One example of a process for the dimerization of isobutene is disclosed in U.S. Pat. No. 6,914,166, in which a $C_4$ olefinic feedstock containing isobutene and n-butene(s) is contacted with dealuminated zeolite beta under conditions including a temperature below 50° C. effective to allow selective dimerization of isobutene to trimethylpentene(s).

U.S. Pat. No. 7,112,711 discloses a process for oligomerizing alkenes having from 3 to 6 carbon atoms, including isobutene, in the presence of a catalyst containing a zeolite of the MFS structure type. The process is carried out at a temperature comprised between 125 and 175° C. when the feedstock contains only alkenes with 3 carbon atoms and between 140 and 240° C. when the feedstock contains at least one alkene with 4 or more carbon atoms.

U.S. Patent Application Publication No. 2007/0213576, published Sep. 13, 2007, discloses a process for the dimerization of isobutene at a temperature in excess of 240° C. in the presence of a multi-dimensional molecular sieve catalyst containing at least one 10 or 12 ring channel, such as ZSM-57, ZSM-5, FAU, Beta, ZSM-12, mordenite, MCM-22 family zeolites, and mixtures thereof to produce a product low in triple-branched octenes.

According to the present invention, it has now been found that EMM-10, a novel molecular sieve of the MCM-22 family, is an effective catalyst for the low temperature selective oligomerization of isobutene in the presence of other $C_4$ alkenes.

SUMMARY

In one aspect, the invention resides in a process for oligomerizing isobutene, the process comprising contacting a feedstock comprising isobutene with a catalyst comprising an EMM-10 molecular sieve under conditions effective to oligomerize said isobutene and produce an effluent containing less isobutene than the feedstock.

Conveniently, said EMM-10 molecular sieve has an X-ray diffraction pattern including d-spacing maxima at 13.18±0.25 and 12.33±0.23 Angstroms, wherein the peak intensity of said d-spacing maximum at 13.18±0.25 Angstroms is at least 90% of the peak intensity of said d-spacing maximum at 12.33±0.23 Angstroms.

In one embodiment, the feedstock also comprises at least one additional $C_4$ alkene, such as butene-1 and/or butene-2.

In a further aspect, the invention resides in a process for selectively dimerizing isobutene in a hydrocarbon feedstock comprising isobutene and at least one additional $C_4$ alkene, the process comprising contacting the feedstock under dimerization conditions with a catalyst comprising a molecular sieve having an X-ray diffraction pattern including d-spacing maxima at 13.18±0.25 and 12.33±0.23 Angstroms, wherein the peak intensity of said d-spacing maximum at 13.18±0.25 Angstroms is at least 90% of the peak intensity of said d-spacing maximum at 12.33±0.23 Angstroms, the process dimerizing at least the isobutene in the feedstock to produce an effluent containing less isobutene than the feedstock.

In one embodiment, the X-ray diffraction pattern said EMM-10 molecular sieve includes d-spacing maxima as listed in the following Table:

| Interplanar d-Spacing (Å) | Relative Intensity, $I/I_o \times 100$ |
|---|---|
| 13.18 ± 0.25 | M-VS |
| 12.33 ± 0.23 | M-VS |
| 11.06 ± 0.18 | W-S |
| 9.25 ± 0.13 | W-S |

In another embodiment, the X-ray diffraction pattern said EMM-10 molecular sieve includes d-spacing maxima as listed in the following Table:

| Interplanar d-Spacing (Å) | Relative Intensity, $I/I_o \times 100$ |
|---|---|
| 13.18 ± 0.25 | M-VS |
| 12.33 ± 0.23 | M-VS |
| 11.06 ± 0.18 | W-S |
| 9.25 ± 0.13 | W-S |
| 3.57 ± 0.06 | W-M |
| 3.43 ± 0.06 | M-VS |

In yet another embodiment, the X-ray diffraction pattern said EMM-10 molecular sieve includes d-spacing maxima as listed in the following Table:

| Interplanar d-Spacing (Å) | Relative Intensity, I/I$_o$ × 100 |
|---|---|
| 13.18 ± 0.25 | M-VS |
| 12.33 ± 0.23 | M-VS |
| 11.06 ± 0.18 | W-S |
| 9.25 ± 0.13 | W-S |
| 6.57 ± 0.15 | W-M |
| 4.41 ± 0.1 | W-M, broad |
| 3.96 ± 0.08 | W-VS, broad |
| 3.57 ± 0.06 | W-M |
| 3.43 ± 0.06 | M-VS |
| 3.34 ± 0.05 | W-S |

Conveniently, said EMM-10 molecular sieve comprises stacked, generally parallel, plate-like crystals, typically such that at least 50 wt % of said crystals have a maximum cross-sectional dimension greater than 1 µm and a thickness less than or equal to 0.025 µm, as measured by SEM.

Conveniently, said conditions include a temperature of about 40° C. to about 200° C., such as about 50° C. to about 100° C., and a pressure of about 700 kPa to about 5000 kPa, such as about 2000 kPa to about 4000 kPa.

Conveniently, the process further comprises using the effluent as a feed in an n-butene oligomerization process or in a process for alkylating benzene to produce sec-butylbenzene, typically after separating the isobutene oligomers from the effluent.

These and other features and attributes of the disclosed process for oligomerizing isobutene of the present disclosure and their advantageous applications and/or uses will be apparent from the detailed description which follows, particularly when read in conjunction with the figures appended hereto.

BRIEF DESCRIPTION OF THE DRAWINGS

To assist those of ordinary skill in the relevant art in making and using the subject matter hereof, reference is made to the appended drawings, wherein.

DETAILED DESCRIPTION

Figure 1:
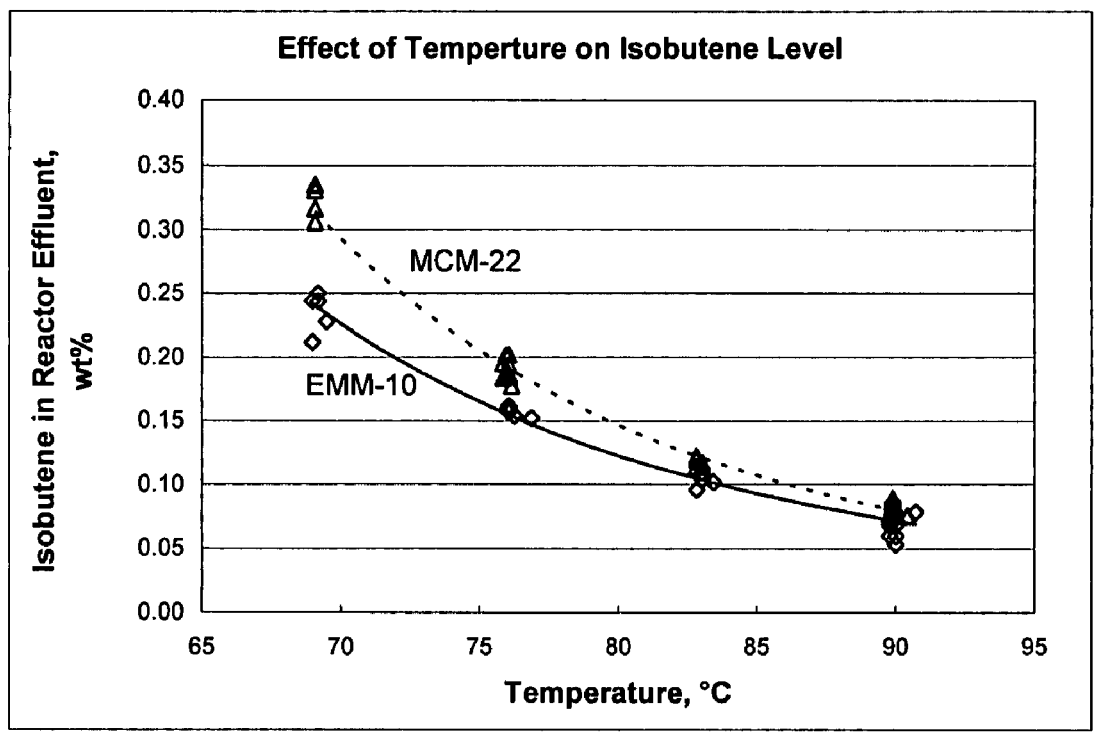
FIG. 1 is a graph plotting temperature against wt % unreacted isobutene in the selective dimerization of a mixed butene feed with a MCM-22 catalyst according to the process of Example 2 and with an EMM-10 catalyst according to the process of Example 3.

As used herein, the numbering scheme for the Periodic Table Groups is used as in Chemical and Engineering News, 63(5), 27 (1985).

Described herein is a process for oligomerizing isobutene in a feedstock wherein the feedstock is contacted with a catalyst comprising an EMM-10 molecular sieve under conditions effective to oligomerize the isobutene and produce an effluent containing less isobutene than the feedstock.

The feedstock can be any process stream containing isobutene, including a pure isobutene stream. In general, however, the feedstock is an olefinic C$_4$ hydrocarbon mixture containing isobutene and at least one linear butene, namely butene-1, cis-butene-2, trans-butene-2 or mixtures thereof. Such olefinic C$_4$ hydrocarbon mixtures can be obtained by steam cracking of ethane, propane, butane, LPG and light naphthas, catalytic cracking of naphthas and other refinery feedstocks and by conversion of oxygenates, such as methanol, to lower olefins. The present oligomerization process then serves to reduce the isobutene concentration of the olefinic C$_4$ hydrocarbon mixture.

For example, the following olefinic C$_4$ hydrocarbon mixtures are generally available in any refinery employing steam cracking to produce olefins: a crude steam cracked butene stream, Raffinate-1 (the product remaining after solvent extraction or hydrogenation to remove butadiene from a crude steam cracked butene stream) and Raffinate-2 (the product remaining after removal of butadiene and isobutene from a crude steam cracked butene stream). Generally, these streams have compositions within the weight ranges indicated in Table 1 below.

TABLE 1

| | | Raffinate 1 | | Raffinate 2 | |
|---|---|---|---|---|---|
| Component | Crude C$_4$ stream | Solvent Extraction | Hydrogenation | Solvent Extraction | Hydrogenation |
| Butadiene | 30-85% | 0-2% | 0-2% | 0-1% | 0-1% |
| C4 acetylenes | 0-15% | 0-0.5% | 0-0.5% | 0-0.5% | 0-0.5% |
| Butene-1 | 1-30% | 20-50% | 50-95% | 25-75% | 75-95% |
| Butene-2 | 1-15% | 10-30% | 0-20% | 15-40% | 0-20% |
| Isobutene | 0-30% | 0-55% | 0-35% | 0-5% | 0-5% |
| N-butane | 0-10% | 0-55% | 0-10% | 0-55% | 0-10% |
| Iso-butane | 0-1% | 0-1% | 0-1% | 0-2% | 0-2% |

Other refinery mixed C$_4$ streams, such as those obtained by catalytic cracking of naphthas and other refinery feedstocks, typically have the following composition:

| Propylene | 0-2 wt % |
|---|---|
| Propane | 0-2 wt % |
| Butadiene | 0-5 wt % |
| Butene-1 | 5-20 wt % |
| Butene-2 | 10-50 wt % |
| Isobutene | 5-25 wt % |
| Iso-butane | 10-45 wt % |
| N-butane | 5-25 wt % |

C$_4$ hydrocarbon fractions obtained from the conversion of oxygenates, such as methanol, to lower olefins more typically have the following composition:

| Propylene | 0-1 wt % |
|---|---|
| Propane | 0-0.5 wt % |
| Butadiene | 0-1 wt % |
| Butene-1 | 10-40 wt % |
| Butene-2 | 50-85 wt % |
| Isobutene | 0-10 wt % |
| N- + iso-butane | 0-10 wt % |

Any one or any mixture of the above C$_4$ hydrocarbon mixtures can be used in the present isobutene oligomerization process.

In addition to other hydrocarbon components, commercial C$_4$ hydrocarbon mixtures typically contain other impurities which could be detrimental to the present oligomerization process or to use of the hydrocarbon mixture downstream of the present oligomerization process. For example, refinery C$_4$ hydrocarbon streams typically contain nitrogen and sulfur impurities, whereas C$_4$ hydrocarbon streams obtained by oxygenate conversion process typically contain unreacted oxygenates and water. Thus, prior to the present oligomerization step, these mixtures may also be subjected to one or more of sulfur removal, nitrogen removal and oxygenate removal. Removal of sulfur, nitrogen, oxygenate impurities is conveniently effected by one or a combination of caustic treatment, water washing, distillation, adsorption using molecular sieves and/or membrane separation. Water is also typically removed by adsorption.

Conveniently, the feed to the present oligomerization process contains less than 1000 ppm, such as less than 500 ppm, for example less than 100 ppm, water. In addition, the feed typically contains less than 100 ppm, such as less than 30 ppm, for example less than 3 ppm, sulfur and less than 10 ppm, such as less than 1 ppm, for example less than 0.1 ppm, nitrogen.

The conditions employed in the present oligomerization process are not closely controlled but in general include a temperature of about 40° C. to about 200° C., such as about 50° C. to about 100° C., and a pressure of about 700 kPa to about 5000 kPa, such as about 2000 kPa to about 4000 kPa. The process can be conducted as a continuous or a batch process, and in the case of the more preferred continuous process, the feed is contacted with the catalyst at a LHSV of about 4 to about 16.

The catalyst employed in the present oligomerization process comprises an EMM-10 molecular sieve, which is a novel molecular sieve of the MCM-22 family. The term "molecular sieve of the MCM-22 family" (or "material of the MCM-22 family" or "MCM-22 family material"), as used herein, includes:

(i) molecular sieves made from a common first degree crystalline building block "unit cell having the MWW framework topology". A unit cell is a-spatial arrangement of atoms which is tiled in three-dimensional space to describe the crystal as described in the "Atlas of Zeolite Framework Types", Fifth Edition, 2001, the entire content of which is incorporated as reference;

(ii) molecular sieves made from a common second degree building block, a 2-dimensional tiling of such MWW framework type unit cells, forming a "monolayer of one unit cell thickness", preferably one c-unit cell thickness;

(iii) molecular sieves made from common second degree building blocks, "layers of one or more than one unit cell thickness", wherein the layer of more than one unit cell thickness is made from stacking, packing, or binding at least two monolayers of one unit cell thick of unit cells having the MWW framework topology. The stacking of such second degree building blocks can be in a regular fashion, an irregular fashion, a random fashion, or any combination thereof; or (iv) molecular sieves made by any regular or random 2-dimensional or 3-dimensional combination of unit cells having the MWW framework topology.

The MCM-22 family materials are generally characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize the molecular sieves are obtained by standard techniques using the K-alpha doublet of copper as the incident radiation and a diffractometer equipped with a scintillation counter and associated computer as the collection system.

Known materials belonging to the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575) and MCM-56 (described in U.S. Pat. No. 5,362,697). The entire contents of the above patents are incorporated herein by reference.

The EMM-10 molecular sieve employed herein is a new member of the MCM-22 family of molecular sieves, the composition and synthesis of which are described in detail in U.S. Provisional Patent Application No. 60/834,030 filed on Jul. 28, 2006, U.S. Provisional Patent Application No. 60/834,001 filed on Jul. 28, 2006, U.S. Provisional Patent Application No. 60/834,032 filed on Jul. 28, 2006, and U.S. Provisional Patent Application No. 60/834,031 filed on Jul. 28, 2006, the entire contents of which are incorporated herein by reference.

In particular, the EMM-10 molecular sieve employed herein has an X-ray diffraction pattern in its as-synthesized form including d-spacing maxima at 13.18±0.25 and 12.33±0.23 Angstroms (Table 2):

TABLE 2

| Interplanar d-Spacing (Å) | Relative Intensity, $I/I_o \times 100$ |
|---|---|
| 13.18 ± 0.25 | M-VS |
| 12.33 ± 0.23 | M-VS | wherein the peak intensity of the d-spacing maximum at 13.18±0.25 Angstroms is at least as great as 90% of, typically at least as great as 100%, even at least as great as 110% of, the peak intensity of the d-spacing maximum at 12.33±0.23 Angstroms.

In some embodiments, the as-synthesized form of the EMM-10 molecular sieve employed herein may have an X-ray diffraction pattern further including d-spacing maxima at 11.06±0.18 and 9.25±0.13 Angstroms (Table 3):

TABLE 3

| Interplanar d-Spacing (Å) | Relative Intensity, $I/I_o \times 100$ |
|---|---|
| 13.18 ± 0.25 | M-VS |
| 12.33 ± 0.23 | M-VS |
| 11.06 ± 0.18 | W-S |
| 9.25 ± 0.13 | W-S | wherein the peak intensity of the d-spacing maximum at 11.06±0.18 Angstroms is at least as great as 90% of, preferably at least as great as 100%, more preferably at least as great as 110% of, the peak intensity of the d-spacing maximum at 9.25±0.13 Angstroms. It is, however, to be appreciated that the d-spacing maxima at 11.1±0.18 and 9.3±0.13 Angstroms may be non-discrete peaks. The term "non-discrete" peaks (also "unresolved" peaks) as used herein means peaks having a monotonic profile in-between them [successive points either consistently increasing (or staying even) or decreasing (or staying even) within noise].

In other embodiments, the as-synthesized form of the EMM-10 molecular sieve employed herein may have an X-ray diffraction pattern including d-spacing maxima as listed in Table 4 or Table 5:

TABLE 4

| Interplanar d-Spacing (Å) | Relative Intensity, I/I$_o$ × 100 |
|---|---|
| 13.18 ± 0.25 | M-VS |
| 12.33 ± 0.23 | M-VS |
| 11.06 ± 0.18 | W-S |
| 9.07 ± 0.13 | W-S |
| 3.57 ± 0.06 | W-M |
| 3.43 ± 0.06 | M-VS |

TABLE 5

| Interplanar d-Spacing (Å) | Relative Intensity, I/I$_o$ × 100 |
|---|---|
| 13.18 ± 0.25 | M-VS |
| 12.33 ± 0.23 | M-VS |
| 11.06 ± 0.18 | W-S |
| 9.07 ± 0.13 | W-S |
| 6.57 ± 0.15 | W-M |
| 4.41 ± 0.1 | W-M, broad |
| 3.96 ± 0.08 | W-VS, broad |
| 3.57 ± 0.06 | W-M |
| 3.43 ± 0.06 | M-VS |
| 3.34 ± 0.05 | W-S |

The EMM-10 molecular sieve employed herein has a composition involving the molar relationship:

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In its as-synthesized form, the material typically has a formula, on an anhydrous basis and in terms of moles of oxides per n moles of YO$_2$, as follows:

$$(0.005-1)M_2O:(1-4)R:X_2O_3:nYO_2$$

wherein M is an alkali or alkaline earth metal, and R is an organic moiety. The M and R components are associated with the material as a result of their presence during synthesis, and are typically removed by post-synthesis methods well known to those skilled in the art and/or hereinafter more particularly described.

The EMM-10 molecular sieve employed in the present process generally exhibits a morphology comprising stacked, generally parallel, plate-like crystals. As measured by Scanning Electron Microscopy (SEM), at least 50 wt %, generally at least 75 wt %, of these crystals have a maximum cross-sectional dimension greater than 1 μm, and at least 50 wt %, generally at least 75 wt %, of the crystals have a thickness less than or equal to 0.025 μm.

In its calcined form, the EMM-10 molecular sieve employed herein typically has a total surface area (sum of the external and the internal surface areas, as measured by the BET method) of greater than 450 m$^2$/g, such as greater than 475 m$^2$/g, and for example, greater than 500 m$^2$/g. In addition, the ratio of the external surface area (as measured by the t-plot of BET method) to the total surface area of the calcined material is generally less than 0.15, such as less than 0.13, or even less than 0.12.

The EMM-10 molecular sieve may be prepared from a hydrothermal reaction mixture containing sources of alkali or alkaline earth metal cation (M), e.g., sodium or potassium, an oxide of trivalent element X, e.g., aluminum, an oxide of tetravalent element Y, e.g., silicon, an organic (R) directing agent, hereinafter more particularly described, and water, the hydrothermal reaction mixture having a composition, in terms of mole ratios of oxides, within the ranges outlined in Table 6:

TABLE 6

| Reactants | Useful | Preferred |
|---|---|---|
| YO$_2$/X$_2$O$_3$ | 10 to infinity | 15-55 |
| H$_2$O/YO$_2$ | 1 to 10000 | 5-35 |
| OH$^-$/YO$_2$ | 0.001-0.59 | 0.1-0.5 |
| M/YO$_2$ | 0.001-2 | 0.1-1 |
| R/YO$_2$ | 0.001-2 | 0.01-0.5 |
| Seed* | 0-25 wt % | 1-5 wt % |
| R | Me$_6$-diquat-5 salt(s) | Me$_6$-diquat-5 salt(s) |

*The weight percent (wt %) of seed is based on the weight of the solid tetrahedral element oxide.

Alternatively, the EMM-10 molecular sieve may be prepared from a hydrothermal reaction mixture having a composition, in terms of mole ratios of oxides, within the ranges outlined in Table 7, wherein M, R X and Y have the same meanings as in Table 6:

TABLE 7

| Reactants | Useful | Preferred |
|---|---|---|
| YO$_2$/X$_2$O$_3$ | 10 to infinity | 15-55 |
| H$_2$O/YO$_2$ | 1 to 10000 | 5-35 |
| OH$^-$/YO$_2$ | 0.76-2 | 0.8-2 |
| M/YO$_2$ | 0.001-2 | 0.1-1 |
| R/YO$_2$ | 0.001-2 | 0.01-0.5 |
| Seed* | 0-25 wt % | 1-5 wt % |
| R | Me$_6$-diquat-5 salt(s) | Me$_6$-diquat-5 salt(s) |

*The weight percent (wt %) of seed is based on the weight of the solid tetrahedral element oxide.

In addition, the EMM-10 molecular sieve may be prepared from a hydrothermal reaction mixture having a composition, in terms of mole ratios of oxides, within the ranges outlined in Table 8, wherein M, R X and Y again have the same meanings as in Table 6:

TABLE 8

| Reactants | Useful | Preferred |
|---|---|---|
| YO$_2$/X$_2$O$_3$ | 10 to infinity | 15-55 |
| H$_2$O/YO$_2$ | 5-35 | 5-30 |
| OH$^-$/YO$_2$ | 0.001-2 | 0.001-2 |
| M/YO$_2$ | 0.001-2 | 0.1-1 |
| R/YO$_2$ | 0.001-2 | 0.01-0.5 |
| Seed* | 0-25 wt % | 1-5 wt % |
| R | Me$_6$-diquat-5 salt(s) | Me$_6$-diquat-5 salt(s) |

*The weight percent (wt %) of seed is based on the weight of the solid tetrahedral element oxide.

In the reaction mixtures defined in Tables 6 to 8, Y is a tetravalent element selected from Groups 4-14 of the Periodic Table of the Elements, such as silicon and/or germanium, preferably silicon. Synthesis of the desired crystalline material is generally favored by the use of a source of YO$_2$ containing at least 30 wt %, especially at least 40 wt %, solid YO$_2$, for example at least 30 wt % solid silica. Suitable commercial grades of silica include those sold by Degussa under the trade names Aerosil or Ultrasil (a precipitated, spray dried silica containing about 90 wt % solid silica), an aqueous colloidal suspension of silica, for example one sold by Grace Davison under the trade name Ludox, or HiSil (a precipitated hydrated $SiO_2$ containing about 87 wt % solid silica, about 6 wt % free $H_2O$ and about 4.5 wt % bound $H_2O$ of hydration and having a particle size of about 0.02 micron.

X is a trivalent element selected from Groups 3-13 of the Periodic Table of the Elements, such as aluminum, and/or boron, and/or iron and/or gallium, especially aluminum. The source of $X_2O_3$, e.g., aluminum, is conveniently aluminum sulphate or hydrated alumina. Other aluminum sources include, for example, other water-soluble aluminum salts, sodium aluminate, or an alkoxide, e.g., aluminum isopropoxide, or aluminum metal, e.g., in the form of chips.

The alkali or alkali earth metal element is advantageously lithium, sodium, potassium, calcium, or magnesium. The source of alkali or alkali earth metal element is advantageously being metal oxide, metal chloride, metal fluoride, metal sulfate, metal nitrate, or metal aluminate. The sodium source advantageously being sodium hydroxide or sodium aluminate. The alkali metal may also be replaced by ammonium ($NH_4^+$) or its equivalents, e.g., alkyl-ammonium ion.

The directing agent R comprises at least one of N, N, N, N'N'N'-hexamethyl-1,5-pentanediaminium ($Me_6$-diquat-5) salt, e.g., $Me_6$-diquat-5 salt of hydroxide, chloride, bromide, fluoride, nitrate, sulfate, phosphate, or any mixture thereof. Suitable $Me_6$-diquat-5 salts include $Me_6$-diquat-5 dibromide, $Me_6$-diquat-5 dichloride, $Me_6$-diquat-5 difluoride, $Me_6$-diquat-5 diiodide, $Me_6$-diquat-5 dihydroxide, $Me_6$-diquat-5 sulfate, $Me_6$-diquat-5 dinitrate, $Me_6$-diquat-5 hydroxide bromide, $Me_6$-diquat-5 hydroxide chloride, $Me_6$-diquat-5 hydroxide fluoride, $Me_6$-diquat-5 hydroxide iodide, $Me_6$-diquat-5 hydroxide nitrate, $Me_6$-diquat-5 fluoride bromide, $Me_6$-diquat-5 fluoride chloride, $Me_6$-diquat-5 fluoride iodide, $Me_6$-diquat-5 fluoride nitrate, $Me_6$-diquat-5 chloride bromide, $Me_6$-diquat-5 chloride iodide, $Me_6$-diquat-5 chloride nitrate, $Me_6$-diquat-5 iodide bromide, $Me_6$-diquat-5 bromide nitrate, and mixtures thereof.

Crystallization of EMM-10 can be carried out at either static or stirred condition in a reactor vessel, such as for example, an autoclave, at a temperature from about 100° C. to about 200° C., such as from about 140° C. to about 180° C., for a time sufficient for crystallization to occur at the temperature used, e.g., from about 1 hour to about 400 hours, such as from about 1 hour to about 200 hours, optionally with agitation of 0-1000 rotations per minutes (RPM), such as 0-400 RPM.

After the crystallization is complete, the crystalline EMM-10 product may be recovered from the remainder of the hydrothermal reaction mixture by, for example, filtering or centrifuging, and may then be washed and dried prior to further treatment to produce the catalyst employed in the present process.

For example, the EMM-10 product of the above synthesis process generally contains water from the reaction mixture and so normally requires at least partial dehydration before being used as, for example, a catalyst. Dehydration is generally achieved by heating the as-synthesized product to a temperature in the range of from about 100° C. to about 600° C. in an atmosphere, such as air, nitrogen, etc. and at atmospheric pressure from between about 1 and about 48 hours. Dehydration can also be performed at room temperature merely by placing the EMM-10 in a vacuum, but a longer time is required to obtain a sufficient amount of dehydration.

The as-synthesized EMM-10 product also contains the or each diquaternary ammonium compound used as the directing agent in it synthesis and hence, prior to use, the product is normally activated by removal of the organic material, leaving active catalytic sites within the microporous channels of the molecular sieve open for contact with a feedstock. The activation process is typically accomplished by heating the as-synthesized EMM-10 product at a temperature of from about 200° C. to about 800° C., normally in the presence of an oxygen-containing gas.

To the extent desired, the original metal cations of the as-synthesized material can be replaced in accordance with techniques well known in the art, at least in part, by ion exchange with other cations. Preferred replacing cations include metal ions, hydrogen ions, hydrogen precursor, e.g., ammonium, ions and mixtures thereof. Particularly preferred cations are those which tailor the catalytic activity for certain hydrocarbon conversion reactions. These include hydrogen, rare earth metals and metals of Groups 1-17, preferably Groups 2-12 of the Periodic Table of the Elements.

In addition, it may be desirable to combine the EMM-10 with another material resistant to the temperatures and other conditions employed in isobutene oligomerization processes. Such materials include catalytically active and inactive materials and synthetic or naturally occurring zeolites as well as inorganic materials such as clays, silica and/or metal oxides. The latter may be either naturally occurring or in the form of gelatinous precipitates or gels including mixtures of silica and metal oxides. Use of a catalytically active material in conjunction with the EMM-10 may improve the conversion and/or selectivity of the catalyst in certain organic conversion processes. Inactive materials suitably serve as diluents to control the amount of conversion in a given process so that products can be obtained economically and without employing other means for controlling the rate of reaction. These materials may be incorporated into naturally-occurring clays, e.g., bentonite and kaolin, to improve the crush strength of the catalyst under commercial operating conditions. Such material, i.e., clays, oxides, etc., function as binders for the catalyst. It is desirable to provide a catalyst having good crush strength because in a petroleum refinery the catalyst is often subjected to rough handling, which tends to break the catalyst down into powder-like materials, which cause problems in processing. These clay binders have been employed for the purpose of improving the crush strength of the catalyst.

Naturally-occurring clays which can be composited with the EMM-10 to produce the catalyst for the present oligomerization process include montmorillonite and kaolin families. These families include subbentonites, and kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the EMM-10 also include inorganic oxides, notably alumina.

In addition to the foregoing materials, the EMM-10 produced by the present process can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The relative proportions of finely divided EMM-10 and inorganic oxide gel matrix vary widely with the EMM-10 content ranging from about 1 to about 90 percent by weight and more usually, particularly when the composite is prepared in the form of beads, in the range from about 2 to about 70 percent by weight of the composite.

The oligomerization process described herein employing EMM-10 as a catalyst is effective in selectively removing isobutene from hydrocarbon feedstocks comprising isobutene and at least one additional $C_4$ alkene and in particular is effective in reducing the isobutene content of a Raffinate-2 stream to less than 0.3 wt %, such as to less than 0.2 wt %, even to less than 0.15 wt %. The resultant isobutene-deficient effluent can then be uses as a feedstock for a linear butene oligomerization process to produce higher ($C_8^+$) olefins or for the alkylation of benzene with linear butenes to produce sec-butylbenzene.

The invention will now be more particularly described with reference to the Examples.

EXAMPLES

Example 1

Preparation of EMM-10

A reaction mixture was prepared having the following composition:

| | |
|---|---|
| DI Water, g | 2500 |
| NaOH, 50%, g | 353.5 |
| $Al_2(SO_4)_3$ (47% solution), g | 505 |
| Ultrasil-PM silica, g | 631.31 |
| 1,5 Bis hexamethylammonium dibromide, 50% solution, g | 1010 |
| Gel Molar Composition: | |
| $SiO_2/Al_2O_3$ | 23 |
| $R/SiO_2$ | 0.15 |
| $OH/SiO_2$ | 0.20 |
| $H_2O/SiO_2$ | 20.5 |
| % Solids ($SiO_2 + Al_2O_3$) | 15 |

After the above reagents were mixed, the mixture was transferred to a 5-gallon autoclave and was stirred at 30 rpm and 160° C. under autogenous pressure for 144 hours, at which time crystallization of the desired EMM-10 was deemed complete. The autoclave was cooled to ambient conditions. The resultant reactor slurry, was collected, filtered, washed with deionized water, and dried at 125° C. overnight. The resultant EMM-10 crystals have a silica to alumina molar ratio of 20.

The dried EMM-10 crystals were combined with Versal 300 alumina in a 65:35 weight ratio crystal to alumina. Water was added to the mixtures to provide a solids level of 44.6% by weight. This combined material was "mull" mixed well using a standard laboratory Muller for sufficient time to create a uniform, activated paste, which was then processed through a 2 inch extruder with die plates or die inserts to give 1/16" diameter cylindrical shaped extrudates. The green extrudates were subsequently dried at 125° C. for a minimum of 8 hours.

After drying, the green extrudates were charged to a muffle pot and placed in a furnace, where the textrudates were heated at 5° F./minute (2.8° C./minute) to 900° F. (482° C.) in 5 v/v $N_2$ and then held at this temperature for 3 hours. The calcined materials were cooled to ambient conditions, removed from the muffle pot and charged to an exchange column. The extrudates were humidified by blowing saturated air over them and then a solution of 1 N $NH_4NO_3$ (2 volume of $NH_4NO_3$ solution per volume of catalyst) was circulated through the column for 2 hours at ambient temperature. The $NH_4NO_3$ solution was replaced with a fresh solution and the exchange repeated until the targeted Na content was achieved. The $NH_4NO_3$ solution was replaced with deionized $H_2O$ and the extrudate was washed. The exchanged extrudates were dried at 250° F. (121° C.) for about 18 hours.

The extrudate was charged to a muffle calciner and heated in 95/5 (v/v) $N_2$/air mix at 10° F./minute (5.6° C./minute) to 800° F. (427° C.). The extrudate was held at 800° F. (427° C.) for 3 hrs, whereafter the temperature was raised to 900° F. (482° C.) and the extrudate was held at this temperature for a further 9 hours. At the end of the further 9 hours, additional air was introduced into the calciner displacing $N_2$, first to produce a 62/38 (v/v) $N_2$/air mix, and then a 38/62 (v/v) $N_2$/air mix, whereafter the extrudate was held at 900° F. (482° C.) for a further 2 hours. After cooling to ambient conditions, the calcined extrudate was submitted for Alpha analysis to determine the acidity of the catalyst. The catalyst was found to have an Alpha value of 350. The Alpha Test is described in U.S. Pat. No. 3,354,078; in the *Journal of Catalysis*, 4, 527 (1965); 6, 278 (1966); and 61, 395 (1980), each incorporated herein by reference as to that description.

Example 2

Selective Isobutene Dimerization with MCM-22 Catalyst

A fresh MCM-22 catalyst with a nominal composition of 65% MCM-22 crystal and 35% Versal 300 alumina was used for the experiment. The catalyst was made by extruding MCM-22 crystal with Versal 300 alumina into 1/16 inch cylindrical form. The extrudate was cut to 1/20 inch lengths and 0.25 g (0.5 cc) of this sized catalyst was used. The catalyst was diluted with sand to 3 cc and loaded into an isothermal, down-flow, fixed-bed, tubular reactor having an outside diameter of 4.76 mm (3/16"). The catalyst was dried at 260° C. and 1 atm (101 kPa) for 2 hours with 100 cc/min flowing nitrogen. Nitrogen was turned off and the reactor was cooled to 69° C. Mixed butenes (see Table 1 for feed composition) was introduced to the reactor at 60 cc/hr until reactor pressure reached 250 psig (1825 kPa). Butene flow was then reduced to 6.0 cc/hr (12 LHSV). Product composition was analyzed online every 4 hours by an HP GC equipped with two parallel columns, a 60M BD-1 column and a 50M PLOT column. Liquid samples were collected daily to ensure material closure. Additional data were collected at 500 psig (3549 kPa) with temperature set at 69, 76, 83, and 90° C. respectively. Representative data are shown in Table 1 and in FIGS. 1 and 2.

TABLE 1

| | | Days on Stream | | | |
|---|---|---|---|---|---|
| | | 16.7 | 18.5 | 19.7 | 23.0 |
| | | Temperature, ° C. | | | |
| | Feed | 69 | 76 | 83 | 90 |
| Composition, wt % | | | | | |
| Isobutane | 0.002 | 0.012 | 0.012 | 0.013 | 0.012 |
| n-Butane | 0.094 | 0.096 | 0.096 | 0.096 | 0.096 |
| t-Butene | 41.285 | 40.610 | 40.527 | 40.575 | 40.522 |
| 1-Butene | 0.092 | 0.098 | 0.104 | 0.164 | 0.223 |
| Isobutene | 4.538 | 0.316 | 0.184 | 0.119 | 0.081 |
| c-Butene | 53.428 | 48.942 | 48.708 | 48.396 | 47.886 |
| Butadiene | 0.477 | 0.433 | 0.409 | 0.381 | 0.343 |
| $C_5$-$C_7$ | 0.083 | 0.195 | 0.199 | 0.199 | 0.201 |
| $C_8$= | 0.000 | 7.621 | 8.200 | 8.515 | 9.018 |
| $C_9^+$ | 0.000 | 1.675 | 1.559 | 1.540 | 1.615 |
| Sum | 100.0 | 100.0 | 100.0 | 100.0 | 100.0 |
| Conversion % | | | | | |
| Isobutene | | 93.0 | 95.9 | 97.4 | 98.2 |
| Butadiene | | 9.2 | 14.3 | 20.1 | 28.1 |
| n-Butenes | | 5.4 | 5.8 | 6.0 | 6.5 |
| Selectivity, wt % | | | | | |
| $C_5$-$C_7$ | | 1.18 | 1.17 | 1.14 | 1.09 |

TABLE 1-continued

|  | | Days on Stream | | | |
|---|---|---|---|---|---|
|  | | 16.7 | 18.5 | 19.7 | 23.0 |
|  | | | Temperature, °C. | | |
|  | Feed | 69 | 76 | 83 | 90 |
| $C_8^=$ | | 81.01 | 83.04 | 83.72 | 83.88 |
| $C_9^+$ | | 17.81 | 15.79 | 15.14 | 15.02 |
| Sum | | 100.0 | 100.0 | 100.0 | 100.0 |

Example 3

Selective Isobutene Dimerization with EMM-10 Catalyst

The extrudate produced in Example 1 was cut into 1/20 inch lengths and 0.25 g (0.5 cc) of this sized catalyst was used. The catalyst was diluted with sand to 3 cc and loaded into an isothermal, down-flow, fixed-bed, tubular reactor having an outside diameter of 4.76 mm (3/16"). The catalyst was dried at 260° C. and 1 atm for 2 hours with 100 cc/min flowing nitrogen. Nitrogen was turned off and the reactor was cooled to 90° C. Mixed butenes (see Table 2 for feed composition) was introduced to the reactor at 60 cc/hr until reactor pressure reached 500 psig (3549 kPa). Butene flow was then reduced to 6.0 cc/hr (12 LHSV). Product composition was analyzed online every 4 hours by an HP GC equipped with two parallel columns, a 60M BD-1 column and a 50M PLOT column. Liquid samples were collected daily to ensure material closure. Data were collected at 90, 83, 76, and 69, and 90° C. respectively. Representative data are shown in Table 2 and in FIGS. 1 and 2.

TABLE 2

|  | | Days om Stream | | | |
|---|---|---|---|---|---|
|  | | 1.9 | 2.6 | 3.9 | 4.9 | 6.1 |
|  | | | Temperature, °C. | | |
|  | Feed | 90 | 83 | 76 | 69 | 90 |
| Composition, wt % | | | | | | |
| Isobutane | 0.002 | 0.012 | 0.012 | 0.012 | 0.012 | 0.012 |
| n-Butane | 0.094 | 0.096 | 0.094 | 0.095 | 0.096 | 0.095 |
| t-Butene | 41.285 | 40.071 | 39.868 | 40.302 | 40.499 | 40.176 |
| 1-Butene | 0.092 | 0.544 | 0.324 | 0.170 | 0.128 | 0.404 |
| Isobutene | 4.538 | 0.071 | 0.104 | 0.159 | 0.244 | 0.085 |
| c-Butene | 53.428 | 45.387 | 46.391 | 47.882 | 48.605 | 46.504 |
| Butadiene | 0.477 | 0.218 | 0.284 | 0.353 | 0.394 | 0.265 |
| $C_5$-$C_7$ | 0.083 | 0.223 | 0.217 | 0.207 | 0.204 | 0.195 |
| $C_8^=$ | 0.000 | 10.880 | 10.376 | 9.087 | 8.355 | 10.212 |
| $C_9^+$ | 0.000 | 2.496 | 2.328 | 1.731 | 1.462 | 2.048 |
| Sum | 100.0 | 100.0 | 100.0 | 100.0 | 100.0 | 100.0 |
| Conversion % | | | | | | |
| Isobutene | | 98.43 | 97.71 | 96.49 | 94.63 | 98.12 |
| Butadiene | | 54.26 | 40.44 | 25.89 | 17.37 | 44.38 |
| n-Butenes Selectivity, wt % | | 9.29 | 8.67 | 6.81 | 5.88 | 8.14 |
| $C_5$-$C_7$ | | 1.03 | 1.04 | 1.13 | 1.21 | 0.90 |
| $C_8^=$ | | 80.50 | 80.83 | 83.05 | 84.07 | 82.55 |

TABLE 2-continued

|  | | Days om Stream | | | |
|---|---|---|---|---|---|
|  | | 1.9 | 2.6 | 3.9 | 4.9 | 6.1 |
|  | | | Temperature, °C. | | |
|  | Feed | 90 | 83 | 76 | 69 | 90 |
| $C_9^+$ | | 18.47 | 18.13 | 15.82 | 14.72 | 16.55 |
| Sum | | 100.0 | 100.0 | 100.0 | 100.0 | 100.0 |

The data in Tables 1 and 2 show that both MCM-22 and EMM-10 are active and selective for conversion of isobutene to dimers or $C_8^=$. The temperature required for the reaction was mild in the range of 69-90° C. Very low levels of isobutene can be obtained by adjusting reaction temperature: 0.24-0.32 wt % at 69° C. and 0.07-0.08 wt % at 90° C.

FIG. 1 shows that EMM-10 was slightly more active than MCM-22 for isobutene removal, in that EMM-10 required a lower temperature than MCM-22 to reduce isobutene to the same level. For example, 69° C. for EMM-10 vs. 72° C. for MCM-22 was required to achieve 0.25 wt % of isobutene in the reactor effluent.

Figure 2:
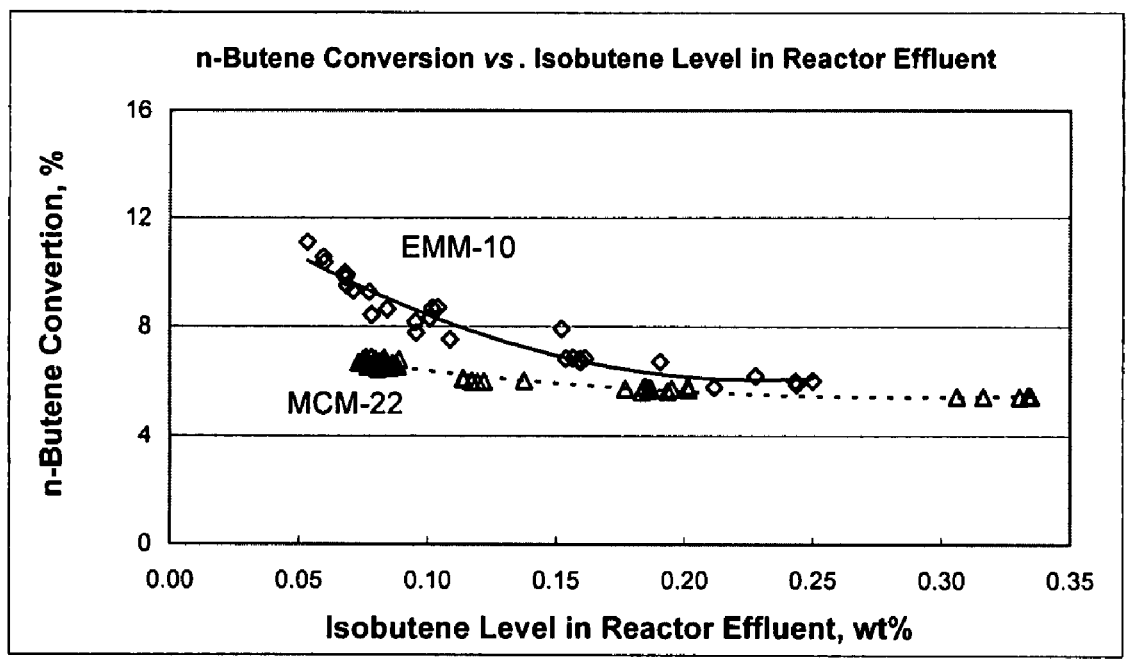
FIG. 2 is a graph plotting n-butene conversion against wt % unreacted isobutene in the selective dimerization of a mixed butene feed with a MCM-22 catalyst according to the process of Example 2 and with an EMM-10 catalyst according to the process of Example 3.

FIG. 2 shows that for each mole of isobutene converted, about 1 mole of n-butene was also converted. It is desirable to have as little n-butene conversion as possible. EMM-10 required higher n-butene conversion than MCM-22 when the target isobutene level was 0.15 wt % or less, but the selectivities were comparable when the target isobutene level was 0.2 wt % or higher.

The data clearly show that EMM-10 is an effective catalyst for isobutene removal from mixed butene feed.

PCT Claims

1. A process for oligomerizing isobutene, the process comprising contacting a feedstock comprising isobutene with a catalyst comprising an EMM-10 molecular sieve under conditions effective to oligomerize said isobutene and produce an effluent containing less isobutene than the feedstock.

2. The process of claim 1 wherein said EMM-10 molecular sieve has an X-ray diffraction pattern including d-spacing maxima at 13.18±0.25 and 12.33±0.23 Angstroms, wherein the peak intensity of said d-spacing maximum at 13.18±0.25 Angstroms is at least 90% of the peak intensity of said d-spacing maximum at 12.33±0.23 Angstroms.

3. The process of claim 2 wherein said X-ray diffraction pattern includes d-spacing maxima as listed in the following Table:

| Interplanar d-Spacing (Å) | Relative Intensity, $I/I_o \times 100$ |
|---|---|
| 13.18 ± 0.25 | M-VS |
| 12.33 ± 0.23 | M-VS |
| 11.06 ± 0.18 | W-S |
| 9.25 ± 0.13 | W-S |

4. The process of claim 2 or claim 3 wherein said X-ray diffraction pattern includes d-spacing maxima as listed in the following Table:

| Interplanar d-Spacing (Å) | Relative Intensity, I/I$_o$ × 100 |
|---|---|
| 13.18 ± 0.25 | M-VS |
| 12.33 ± 0.23 | M-VS |
| 11.06 ± 0.18 | W-S |
| 9.25 ± 0.13 | W-S |
| 3.57 ± 0.06 | W-M |
| 3.43 ± 0.06 | M-VS |

5. The process of any one of claims 2 to 4 wherein said X-ray diffraction pattern includes d-spacing maxima as listed in the following Table:

| Interplanar d-Spacing (Å) | Relative Intensity, I/I$_o$ × 100 |
|---|---|
| 13.18 ± 0.25 | M-VS |
| 12.33 ± 0.23 | M-VS |
| 11.06 ± 0.18 | W-S |
| 9.25 ± 0.13 | W-S |
| 6.57 ± 0.15 | W-M |
| 4.41 ± 0.1 | W-M, broad |
| 3.96 ± 0.08 | W-VS, broad |
| 3.57 ± 0.06 | W-M |
| 3.43 ± 0.06 | M-VS |
| 3.34 ± 0.05 | W-S |

6. The process of any preceding claim wherein said EMM-10 molecular sieve comprises stacked, generally parallel, plate-like crystals.

7. The process of claim 6 wherein at least 50 wt % of said crystals have a maximum cross-sectional dimension greater than 1 μm as measured by SEM.

8. The process of claim 6 or claim 7 wherein at least 50 wt % of said crystals have a thickness less than or equal to 0.025 μm as measured by SEM.

9. The process of any preceding claim wherein said conditions include a temperature of 40° C. to 200° C., preferably 50° C. to 100° C.

10. The process of any preceding claim wherein said conditions include a pressure of 700 kPa to 5000 kPa, preferably 2000 kPa to 4000 kPa.

11. The process of any preceding claim wherein the feedstock also comprises at least one additional C$_4$ alkene.

12. The process of any preceding claim wherein the feedstock also comprises butene-1 and/or butene-2.

13. The process of claim 12 and further comprising using said effluent as a feedstock in the alkylation of benzene to produce sec-butylbenzene.

14. The process of claim 12 and further comprising using said effluent as a feedstock for oligomerization to produce higher olefins.

Applicants have attempted to disclose all embodiments and applications of the disclosed subject matter that could be reasonably foreseen. However, there may be unforeseeable, insubstantial modifications that remain as equivalents. While the present disclosure has been described in conjunction with specific, exemplary embodiments thereof, it is evident that many alternations, modifications, and variations will be apparent to those skilled in the art in light of the foregoing description without departing from the spirit or scope of the present disclosure. Accordingly, the present disclosure is intended to embrace all such alterations, modifications, and variations of the above detailed description. All patents and other documents cited herein, including priority documents, are fully incorporated by reference to the extent such disclosure is not inconsistent with this disclosure and for all jurisdictions in which such incorporation is permitted. When numerical lower limits and numerical upper limits are listed herein, ranges from any lower limit to any upper limit are contemplated.

What is claimed is:

1. A process for oligomerizing isobutene, the process comprising contacting a feedstock comprising isobutene with a catalyst comprising an EMM-10 molecular sieve under conditions effective to oligomerize said isobutene and produce an effluent containing less isobutene than the feedstock.

2. The process of claim 1 wherein said EMM-10 molecular sieve has an X-ray diffraction pattern including d-spacing maxima at 13.18±0.25 and 12.33±0.23 Angstroms, wherein the peak intensity of said d-spacing maximum at 13.18±0.25 Angstroms is at least 90% of the peak intensity of said d-spacing maximum at 12.33±0.23 Angstroms.

3. The process of claim 2 wherein said X-ray diffraction pattern includes d-spacing maxima as listed in the following Table:

| Interplanar d-Spacing (Å) | Relative Intensity, I/I$_o$ × 100 |
|---|---|
| 13.18 ± 0.25 | M-VS |
| 12.33 ± 0.23 | M-VS |
| 11.06 ± 0.18 | W-S |
| 9.25 ± 0.13 | W-S. |

4. The process of claim 2 wherein said X-ray diffraction pattern includes d-spacing maxima as listed in the following Table:

| Interplanar d-Spacing (Å) | Relative Intensity, I/I$_o$ × 100 |
|---|---|
| 13.18 ± 0.25 | M-VS |
| 12.33 ± 0.23 | M-VS |
| 11.06 ± 0.18 | W-S |
| 9.25 ± 0.13 | W-S |
| 3.57 ± 0.06 | W-M |
| 3.43 ± 0.06 | M-VS. |

5. The process of claim 2 wherein said X-ray diffraction pattern includes d-spacing maxima as listed in the following Table:

| Interplanar d-Spacing (Å) | Relative Intensity, I/I$_o$ × 100 |
|---|---|
| 13.18 ± 0.25 | M-VS |
| 12.33 ± 0.23 | M-VS |
| 11.06 ± 0.18 | W-S |
| 9.25 ± 0.13 | W-S |
| 6.57 ± 0.15 | W-M |
| 4.41 ± 0.1 | W-M, broad |
| 3.96 ± 0.08 | W-VS, broad |
| 3.57 ± 0.06 | W-M |
| 3.43 ± 0.06 | M-VS |
| 3.34 ± 0.05 | W-S. |

6. The process of claim 1 wherein said EMM-10 molecular sieve comprises stacked, generally parallel, plate-like crystals.

7. The process of claim 6 wherein at least 50 wt % of said crystals have a maximum cross-sectional dimension greater than 1 μm as measured by SEM.

8. The process of claim 6 wherein at least 50 wt % of said crystals have a thickness less than or equal to 0.025 μm as measured by SEM.

9. The process of claim 1 wherein the feedstock also comprises at least one additional $C_4$ alkene.

10. The process of claim 1 wherein the feedstock also comprises butene-1 and/or butene-2.

11. The process of claim 1 wherein said conditions include a temperature of about 40° C. to about 200° C.

12. The process of claim 1 wherein said conditions include a temperature of about 50° C. to about 100° C.

13. The process of claim 1 wherein said conditions include a pressure of about 700 kPa to about 5000 kPa.

14. The process of claim 1 wherein said conditions include a pressure of about 2000 kPa to about 4000 kPa.

15. A process for selectively dimerizing isobutene in a hydrocarbon feedstock comprising isobutene and at least one additional $C_4$ alkene, the process comprising contacting the feedstock under dimerization conditions with a catalyst comprising an EMM-10 molecular sieve having an X-ray diffraction pattern including d-spacing maxima at 13.18±0.25 and 12.33±0.23 Angstroms, wherein the peak intensity of said d-spacing maximum at 13.18±0.25 Angstroms is at least 90% of the peak intensity of said d-spacing maximum at 12.33±0.23 Angstroms, the process dimerizing at least the isobutene in the feedstock to produce an effluent containing less isobutene than the feedstock.

16. The process of claim 15 wherein said X-ray diffraction pattern includes d-spacing maxima as listed in the following Table:

| Interplanar d-Spacing (Å) | Relative Intensity, $I/I_o \times 100$ |
|---|---|
| 13.18 ± 0.25 | M-VS |
| 12.33 ± 0.23 | M-VS |
| 11.06 ± 0.18 | W-S |
| 9.25 ± 0.13 | W-S. |

17. The process of claim 15 wherein said X-ray diffraction pattern includes d-spacing maxima as listed in the following Table:

| Interplanar d-Spacing (Å) | Relative Intensity, $I/I_o \times 100$ |
|---|---|
| 13.18 ± 0.25 | M-VS |
| 12.33 ± 0.23 | M-VS |
| 11.06 ± 0.18 | W-S |
| 9.25 ± 0.13 | W-S |
| 3.57 ± 0.06 | W-M |
| 3.43 ± 0.06 | M-VS. |

18. The process of claim 15 wherein said X-ray diffraction pattern includes d-spacing maxima as listed in the following Table:

| Interplanar d-Spacing (Å) | Relative Intensity, $I/I_o \times 100$ |
|---|---|
| 13.18 ± 0.25 | M-VS |
| 12.33 ± 0.23 | M-VS |
| 11.06 ± 0.18 | W-S |
| 9.25 ± 0.13 | W-S |
| 6.57 ± 0.15 | W-M |
| 4.41 ± 0.1 | W-M, broad |
| 3.96 ± 0.08 | W-VS, broad |
| 3.57 ± 0.06 | W-M |
| 3.43 ± 0.06 | M-VS |
| 3.34 ± 0.05 | W-S. |

19. The process of claim 15 wherein said conditions include a temperature of about 40° C. to about 200° C.

20. The process of claim 15 wherein said conditions include a temperature of about 50° C. to about 100° C.

21. The process of claim 15 wherein the feedstock also comprises butene-1 and/or butene-2.

22. The process of claim 21 and further comprising using said effluent as a feedstock in the alkylation of benzene to produce sec-butylbenzene.

23. The process of claim 21 and further comprising using said effluent as a feedstock for oligomerization to produce higher olefins.

\* \* \* \* \*